(12) United States Patent
Tan et al.

(10) Patent No.: US 7,709,658 B2
(45) Date of Patent: May 4, 2010

(54) PROCESS FOR SYNTHESIZING A SUBSTITUTED PYRAZOLE

(75) Inventors: Lushi Tan, Edison, NJ (US); James Christopher McWilliams, Hoboken, NJ (US); Frederick W. Hartner, Somerville, NJ (US); Naoki Yoshikawa, Edison, NJ (US); Wenji Li, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 159 days.

(21) Appl. No.: 11/988,849

(22) PCT Filed: Jul. 21, 2006

(86) PCT No.: PCT/US2006/028545

§ 371 (c)(1),
(2), (4) Date: Jan. 15, 2008

(87) PCT Pub. No.: WO2007/015999

PCT Pub. Date: Feb. 8, 2007

(65) Prior Publication Data

US 2009/0054662 A1    Feb. 26, 2009

Related U.S. Application Data

(60) Provisional application No. 60/702,454, filed on Jul. 26, 2005.

(51) Int. Cl.
*C07D 231/10* (2006.01)
*C07D 231/12* (2006.01)

(52) U.S. Cl. .................. 548/376.1; 548/377.1

(58) Field of Classification Search .......... None
See application file for complete search history.

(56) References Cited

U.S. PATENT DOCUMENTS

| | | | |
|---|---|---|---|
| 5,670,503 A | 9/1997 | Kawai et al. |
| 5,776,954 A | 7/1998 | de Laszlo et al. |
| 6,218,431 B1 | 4/2001 | Schoen et al. |
| 6,420,427 B1 | 7/2002 | Takahashi et al. |
| 6,503,949 B1 | 1/2003 | Lau et al. |
| 6,562,807 B2 | 5/2003 | Jorgensen et al. |
| 6,613,942 B1 | 9/2003 | Ling et al. |
| 6,762,318 B2 | 7/2004 | Kodra et al. |
| 6,881,746 B2 | 4/2005 | Lau et al. |
| 2005/0171196 A1 | 8/2005 | Fujii et al. |
| 2005/0272794 A1* | 12/2005 | Parmee et al. ............. 514/406 |
| 2006/0084681 A1 | 4/2006 | Parmee et al. |
| 2007/0088070 A1 | 4/2007 | Parmee et al. |

FOREIGN PATENT DOCUMENTS

| | | |
|---|---|---|
| RU | 2124517 | 1/1999 |
| RU | 2001110360 | 3/2003 |
| WO | WO 97/16442 | 5/1997 |
| WO | WO 98/04528 | 2/1998 |
| WO | WO 98/21957 | 5/1998 |
| WO | WO 98/22108 | 5/1998 |
| WO | WO 98/22109 | 5/1998 |
| WO | WO 99/32448 | 7/1999 |
| WO | WO 00/15229 | 3/2000 |
| WO | WO 00/39088 | 7/2000 |
| WO | WO 00/69810 | 11/2000 |
| WO | WO 02/00612 | 1/2002 |
| WO | WO 02/08188 A1 | 1/2002 |
| WO | WO 02/40444 A1 | 5/2002 |
| WO | WO 03/048109 | 6/2003 |
| WO | WO 03 051357 A1 | 6/2003 |
| WO | WO 03/053938 A1 | 7/2003 |
| WO | WO 03/064404 | 8/2003 |
| WO | WO 03/097619 | 11/2003 |
| WO | WO 2004/002480 | 1/2004 |
| WO | WO 2004/009158 | 1/2004 |
| WO | WO 2004/050039 A2 | 6/2004 |
| WO | WO 2004/069158 A2 | 8/2004 |
| WO | WO 2004/092146 A2 | 10/2004 |
| WO | WO 2004/100875 A2 | 11/2004 |
| WO | WO 2005/121097 A2 | 12/2005 |

OTHER PUBLICATIONS

M. J. Burk et al., "Catalytic Asymmetric Reductive Amination of Ketones via Highly Enantioselective Hydrogenation ofthe C=N Double Bond", Tetrahedron, vol. 50, No. 15, pp. 4399-4428 (1994).
Kurukulasuriya et al., "Biaryl amide glucagon receptor antagonists", Bioorganic & Medicinal Chemistry Letter, vol. 114, pp. 2047-2050 (2004).
Merck & Co., Inc., U.S. Appl. No. 60/442,828, filed Jan. 27, 2003.
Merck & Co., Inc., U.S. Appl. No. 60/577,116, filed Jun. 4, 2004.

* cited by examiner

*Primary Examiner*—Rebecca L Anderson
*Assistant Examiner*—Matthew P Coughlin
(74) *Attorney, Agent, or Firm*—Richard C. Billups; John C. Todaro

(57) ABSTRACT

The present invention relates to substituted pyrazoles, compositions containing such compounds and methods of treatment. The compounds are glucagon receptor antagonists and thus are useful for treating, preventing or delaying the onset of type 2 diabetes mellitus.

3 Claims, No Drawings

PROCESS FOR SYNTHESIZING A SUBSTITUTED PYRAZOLE

CROSS-REFERENCE TO RELATED APPLICATIONS

This application is a U.S. National Phase application under 35 U.S.C. §371 of PCT Application No. PCT/US2006/028545, filed Jul. 21, 2006, which published as WO 2007/015999 on Feb. 8, 2007, and claims priority under 35 U.S.C. §119 from U.S. Provisional Application No. 60/702,454, filed Jul. 26, 2005.

BACKGROUND OF THE INVENTION

The present invention relates to a process for synthesizing a substituted pyrazole. The compound is particularly useful as an anti-diabetic compound. In particular, the compound has demonstrated activity as a glucagon receptor antagonist.

Glucagon serves as the major regulatory hormone attenuating the effect of insulin in its inhibition of liver gluconeogenesis and is normally secreted by α-cells in pancreatic islets in response to falling blood glucose levels. The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly.

In addition to elevated levels of circulating insulin, type II diabetics have elevated levels of plasma glucagon and increased rates of hepatic glucose production. The compound that is the subject of the process described herein in an antagonist of glucagon, and thus useful in improving insulin responsiveness in the liver, decreasing the rate of gluconeogenesis and lowering the rate of hepatic glucose output resulting in a decrease in the levels of plasma glucose.

One object of the present invention is to provide a process wherein the protecting groups are easily removed without resort to harsh deprotection conditions.

Another object of the present invention is to provide a process which facilitates selective deprotection.

These and other objects will be apparent from the teachings contained herein.

SUMMARY OF THE INVENTION

The present invention involves a process of synthesizing a compound of formula I:

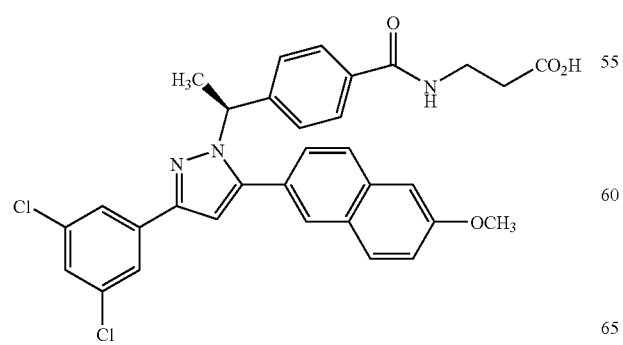

I or a pharmaceutically acceptable salt or solvate thereof, comprising reacting a compound of formula III:

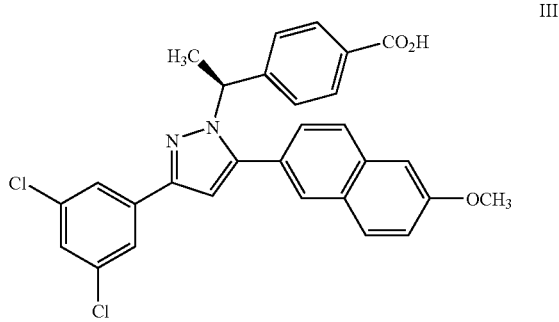

III with 1,1'-carbonyldiimidazole and a beta alanine ester or a salt or solvate thereof, and hydrolyzing with a base to provide a compound of formula I.

DETAILED DESCRIPTION OF THE INVENTION

The invention is described in connection with the following abbreviatons and definitions.

| | |
|---|---|
| Bu = butyl, t-Bu = t-butyl | Bn and Bnzl = benzyl |
| BOC, Boc = t-butyloxycarbonyl | CBZ, Cbz = Benzyloxycarbonyl |
| CDI = carbonyldiimidazole | |
| COD = cyclooctadiene | $C_6H_{11}$ = cyclohexyl |
| DCC = Dicyclohexylcarbodiimide | DCM = dichloromethane |
| DMAC = dimethylacetamide | DMF = N,N-dimethylformamide |
| DMAP = 4-Dimethylaminopyridine | Et = ethyl |
| EtOAc = ethyl acetate | EtOH = ethanol |
| Fc = ferrocenyl | IPA = isopropanol |
| HOAc = acetic acid | TFA = Trifluoroacetic acid |
| Me = methyl | Py, Pyr = pyridyl |
| Ph = phenyl | IPAc = isopropylacetamide |
| THF = Tetrahydrofuran | NMP = N-methyl pyrrolidone |

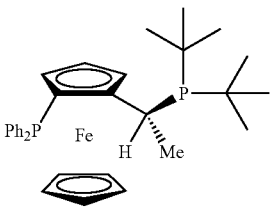

$Ph_2$-Fc-P-$(tBu)_2$

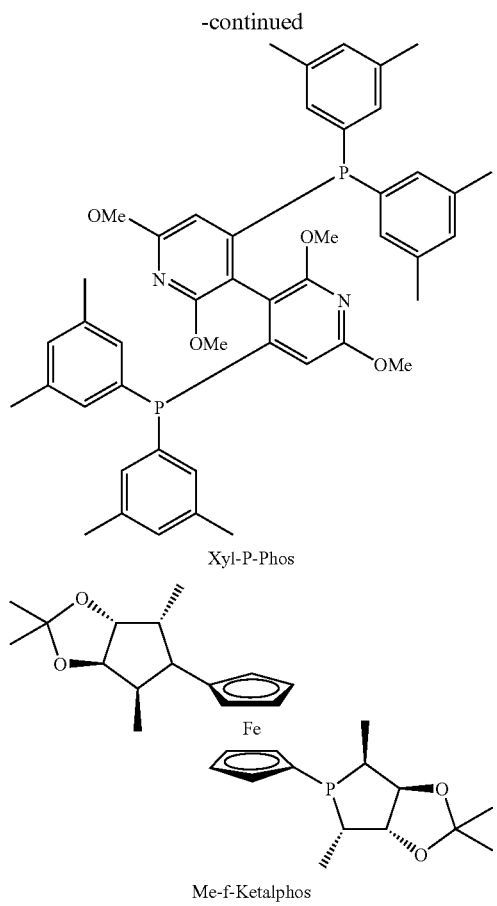

Xyl-P-Phos

Me-f-Ketalphos

Ph$_2$-Fc-P-(tBu)$_2$ is a Josiphos ligand which is disclosed in U.S. Pat. No. 6,777,567B2 (Solvias) and commercially available from Strem. Xyl-P-Phos is disclosed in U.S. Pat No. 5,886,182 (Synetix) and commercially available from Strem. Me-f-Ketal phos is similarly commercially available from Chiral Quest. A variety of Rh based catalysts may be used as well.

The compound described herein may be prepared according to the methodology outlined in the following general synthetic schemes.

SCHEME 1

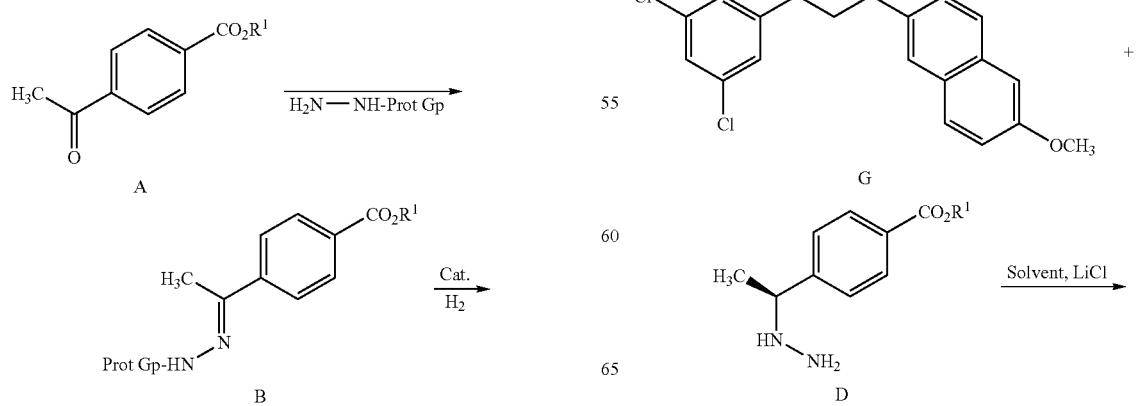

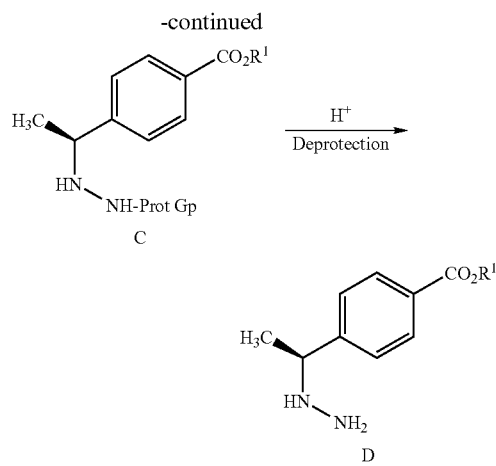

SCHEME 2

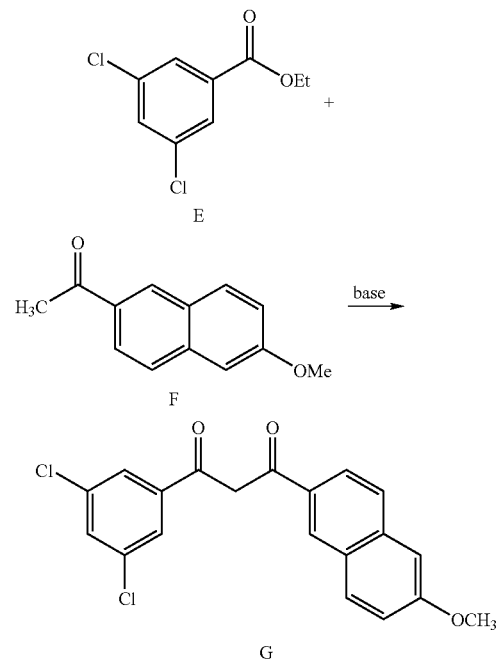

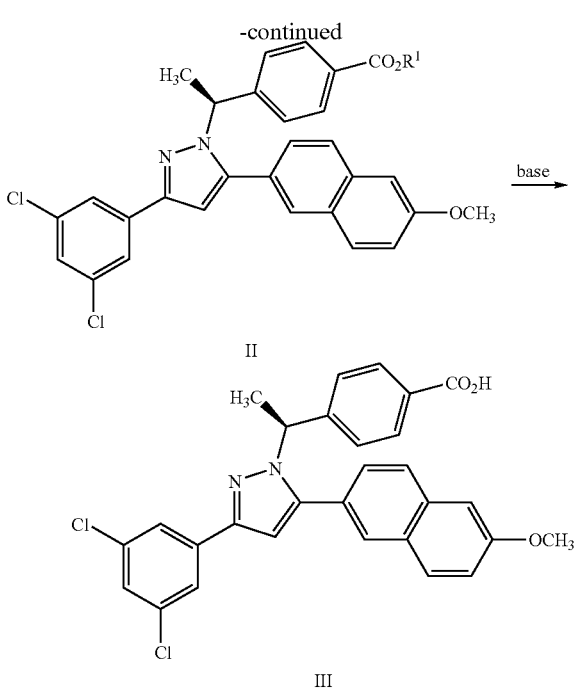

condensation reaction is conducted in a suitable solvent, such as toluene, under acidic conditions, with for example, acetic acid, at about 60 degrees C.

The protected hydrazone B is asymmetrically hydrogenated using a hydrogen source, such as hydrogen gas, and a catalyst to produce a chiral N-protected-hydrazine C. This hydrazine is produced in enantiomeric excess (approximately 86% ee). A suitable catalyst for this conversion is a precatalyst, such as $Rh(COD)BF_4$ mixed with a suitable ligand, such as Josiphos.

Deprotection of the protecting group in C and subsequent enantiomeric excess upgrade using benzene sulfonic acid in ethanol provides a crystalline hydrazine D as the benzenesulfonate salt (not shown), with greater than 99% enantiomeric excess.

With reference to Scheme 2, the 1,3-dione G is prepared by condensation of ester E and ketone F in the presence of a base, such as potassium t-butoxide. Cyclization between D and G can then be undertaken in a suitable solvent, such as DMAc, NMP and the like, in the presence of an additive. Suitable examples of additives include LiCl, LiBr, $MgBr_2$ and other Lewis acids. Alternatively, tetrabutyl ammonium chloride can be used. The additive provides high regioselectivity, as high as about 17:1. The ester forming moiety of compound II is thereafter hydrolyzed with a suitable base, for example, NaOH, to produce acid III.

As shown with reference to Scheme 3, acid III can then be combined with a beta alanine ester, or a salt or solvate thereof,

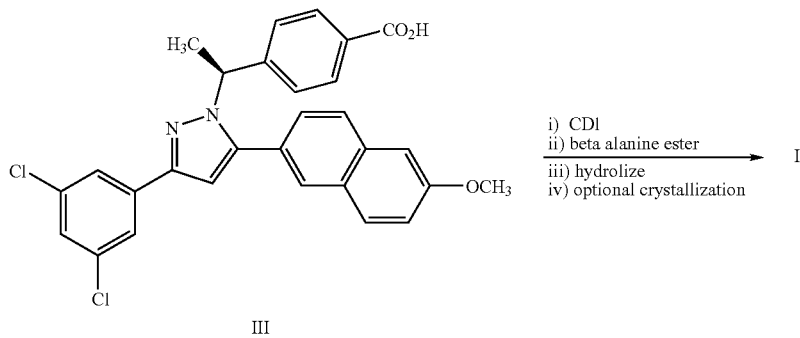

Within the schemes above, $R^1$ represents a suitable ester forming group. Examples include $C_{1-10}$ alkyl, such as ethyl, isopropyl, t-butyl, t-butylcyclohexyl and the like, and benzyl. Preferred is ethyl.

Similarly, the notation Prot Gp-hydrazine refers to a protected hydrazine, protected with a suitable protecting group, designated Prot Gp, which represents the protecting group. Examples include t-butoxycarbonyl, methoxycarbonyl, carboxybenzoyl, benzyl and the like.

Many of the intermediates contain an asymmetric center and thus occur as racemates and mixtures thereof. The present invention therefore includes all such isomeric forms of the compounds, in pure form as well as in mixtures.

The process described herein is generally considered a stereospecific synthesis. Ketone A is condensed with a protected hydrazine to produce a protected hydrazone B. This preferably the HCl salt, to form the beta alanyl ester of III (not shown). This ester may then be hydrolyzed, such as with additional base, for example, NaOH, and optionally crystallized, such as from acetonitrile and water, to produce the title compound I as a free acid.

An alternative process for the synthesis of compounds of formula II is shown below in Scheme 4.

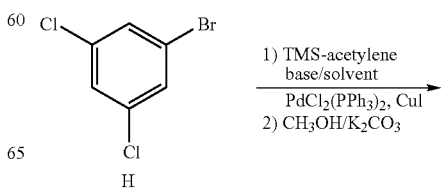

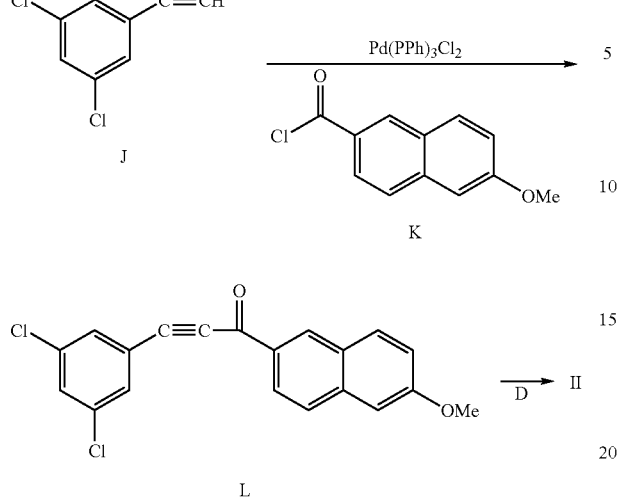

Briefly, 3,5-dichlorophenylacetylene J is produced by displacing bromine from bromo-3,5-dichlorobenzene H. Such reactions are typically conducted under an inert atmosphere, in base, e.g., triethylamine in a suitable solvent. This intermediate is reacted with 6-methoxy-2-naphthoic acid chloride K to produce an acetylenic ketone L. The acetylenic ketone L is thereafter reacted with the chiral hydrazine D to produce the chiral intermediate II. Compound II is thereafter incorporated into the synthesis described above with respect to Scheme 3, reacting with a beta alanyl ester and then hydrolyzing to produce the target compound I.

Dose Ranges

The daily dosage range for the compound of formula I is within the general range of from about 0.001 mg to about 1000 mg, in single or divided doses. It may be necessary to use dosages outside of these limits in some cases.

Representative dosages for adults thus range from about 0.1 mg to about 1.0 g per day, preferably about 1 mg to about 200 mg, in single or divided doses.

Pharmaceutical Compositions

Pharmaceutical compositions comprise a compound of Formula I or a pharmaceutically acceptable salt or solvate thereof and a pharmaceutically acceptable carrier. This encompasses a product comprising the active compound and one or more inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients.

While the invention has been described and illustrated with reference to specific embodiments, numerous changes, modifications, and substitutions can be made therein without departing from the spirit and scope of the invention. It is intended therefore that the invention be limited only by the scope of the claims which follow and that such claims be interpreted as broadly as is reasonable.

What is claimed is:

1. A process for the synthesis of a compound of formula I:

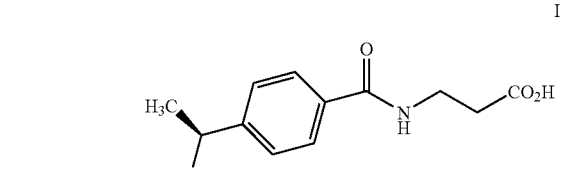

comprising reacting a compound of formula III:

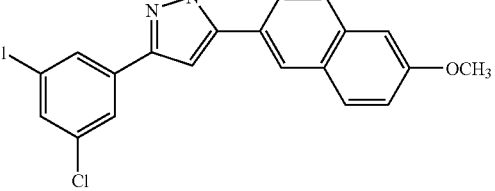

in the presence of 1,1'-carbonyldiimidazole with an ester of beta-alanine or a salt thereof or solvate thereof to produce an ester of formula II:

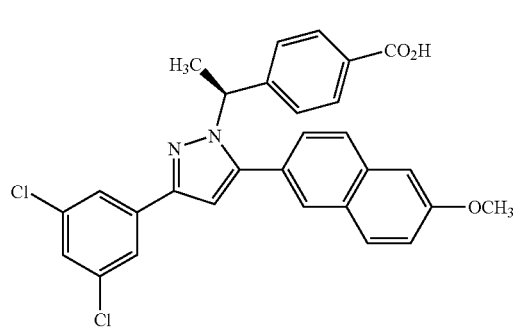

wherein $R^1$ represents an ester forming group, and hydrolyzing the ester of formula II with a base to provide a compound of formula I.

2. A process for the synthesis of a compound of formula II:

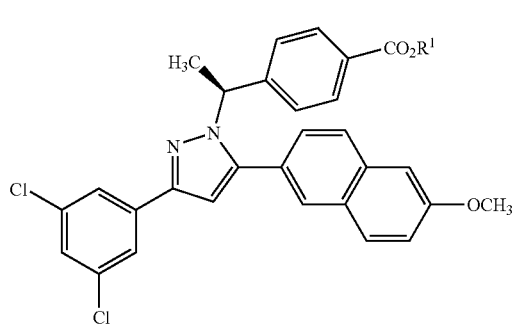

wherein $R^1$ represents an ester forming group, comprising reacting a compound of formula G:

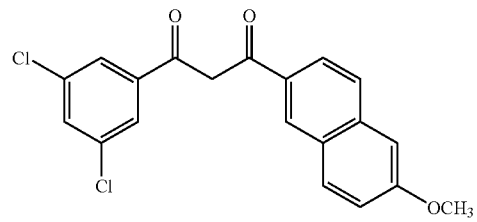

and a compound of formula D:

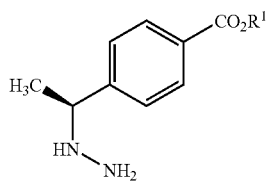

to produce a compound of formula II.

3. A process for the synthesis of a compound of formula I:

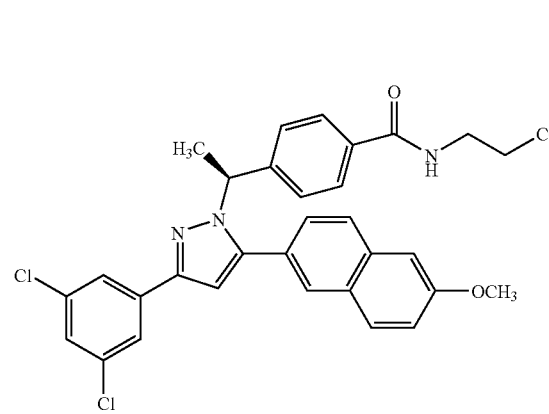

comprising:

(a) reacting compounds of formulas E and F:

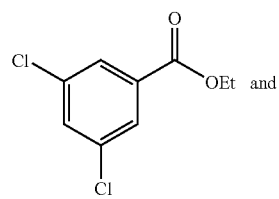

in the presence of potassium t-butoxide to produce a compound of formula G:

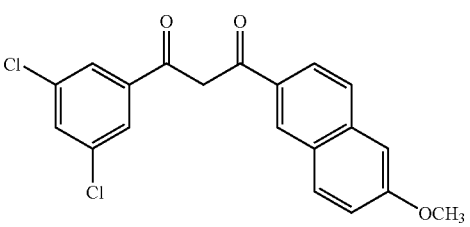

(b) reacting the compound of formula G with a compound of formula D:

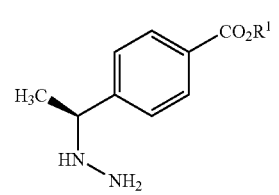

wherein R¹ represents an ester forming group, to produce a compound of formula II:

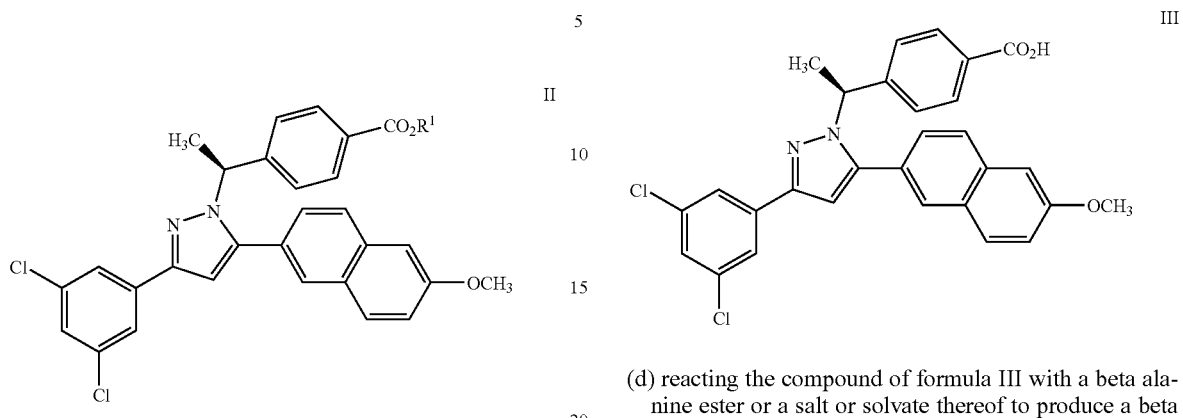

(c) hydrolyzing the compound of formula II with a base to produce a compound of formula III:

(d) reacting the compound of formula III with a beta alanine ester or a salt or solvate thereof to produce a beta alanyl ester of the compound of formula III, and (e) hydrolyzing the beta alanyl ester of the compound of formula III to produce a compound of formula I.

* * * * *